United States Patent

Poole

[11] Patent Number: 5,847,294
[45] Date of Patent: Dec. 8, 1998

[54] APPARATUS FOR DETERMINING POWDER FLOWABILITY

[75] Inventor: Trent A. Poole, So. Amherst, Mass.

[73] Assignee: Amherst Process Instruments, Inc., Amherst, Mass.

[21] Appl. No.: 629,446

[22] Filed: Apr. 9, 1996

[51] Int. Cl.$^6$ ............ G01N 11/00; G01N 11/02; G01N 11/14; G01N 15/00
[52] U.S. Cl. .............. 73/866; 73/54.32; 73/624; 250/559.22; 250/574; 366/56; 366/63; 356/376
[58] Field of Search .................... 73/866, 865.5, 73/624, 54.02, 54.23–54.35, 105, 290 V, 291, 863, 864.91; 356/376; 250/573, 574, 576, 577, 559.22; 366/56, 63

[56] References Cited

U.S. PATENT DOCUMENTS

| H503 | 8/1988 | Keller | 250/574 X |
|---|---|---|---|
| 938,201 | 10/1909 | Aeschbach | 366/56 X |
| 1,236,706 | 8/1917 | Grosvenor | 37/54.33 |
| 2,722,408 | 11/1955 | Hilkemeier | 366/63 |
| 3,380,293 | 4/1968 | Murphy | 73/624 |
| 4,181,023 | 1/1980 | Clamroth et al. | 73/866 |
| 4,274,286 | 6/1981 | Gioia | 73/866 |
| 4,886,714 | 12/1989 | Torii et al. | 428/694 BH |
| 4,895,034 | 1/1990 | Poole | 73/865.5 |
| 5,109,717 | 5/1992 | Galetto et al. | 73/866 |
| 5,480,626 | 1/1996 | Klasen et al. | 423/449.1 |
| 5,522,555 | 6/1996 | Poole | 241/33 |

FOREIGN PATENT DOCUMENTS

| 252723 | 9/1969 | U.S.S.R. | 73/54.02 |
|---|---|---|---|
| 478192 | 7/1975 | U.S.S.R. | 73/866 |
| 1392453 | 4/1988 | U.S.S.R. | 73/54.35 |
| 1571467 | 6/1990 | U.S.S.R. | 73/54.24 |
| 1244408 | 9/1971 | United Kingdom | 73/54.32 |
| 2091117 | 7/1982 | United Kingdom | 366/56 |

OTHER PUBLICATIONS

Rheologica Acta, Band 8, Heft 2 (1969) pp. 184–187 "Calibration and use of the Epprecht Rheomat" G. Hartley et al.

Dr. Brian H. Kaye, Fractal Dimensions in Data Space; New Descriptors for Fineparticle Systems, Particle and Particle Systems Characterization, vol. 10, 1993, pp. 191–200.

Dr. Brian H. Kaye and Remi Trottier, "The Many Measurements of Fine Particles", Chemical Engineering, Apr. 1995, pp. 78–86.

(List continued on next page.)

Primary Examiner—Thomas P. Noland
Attorney, Agent, or Firm—Wolf, Greenfield & Sacks, P.C.

[57] ABSTRACT

Apparatus for determining flowability of a powder by sensing powder avalanching includes a sample drum having a generally cylindrical sample chamber for holding a powder sample, a support frame including a drum shaft for supporting the sample drum for rotation, a drive motor and a drive mechanism coupled between the drive motor and the drum shaft such that the drum rotates when the drive motor is energized. The apparatus further includes an avalanche sensor for sensing avalanching of the powder sample within the sample chamber as the sample drum rotates. The avalanche sensor may be implemented as a backlash sensor for sensing intermittent reverse angular displacement of the sample drum caused by avalanching of the powder sample. A torque loading sensor may also be used to sense avalanching of the powder sample. A controlled gas may be circulated through the sample chamber by a gas conditioning system. The gas in the sample chamber can be measured and/or controlled. The apparatus may include a vibration mechanism for vibrating the sample drum.

12 Claims, 14 Drawing Sheets

OTHER PUBLICATIONS

Dr. Brian H. Kaye, et al. "Update on the Development of an Expert System for use in Powder Tech. Studies", Proceedings of the Powder and Bulk Solids Conference, Rosemont, IL, May 8–11, 1995 9 pages.

Dr. Brian H. Kaye, et al. "Comparison of the Perf. of Various Sieving Surfaces with Regard in the Develop. of Miniatures Sieves", Proc. of the Powder and Bulk Solids Conf., Rosemont, IL, May 8–11, 1995 pp. 347–402.

Dr. Brian H. Kaye, "A New Approach to Powder Rheology", Pharmaceutical Technology, vol. 15, No. 9, Mar. 1994 5 pages.

Dr. Brian H. Kaye, "Measuring Parameters Relevant to the Flow and Packing of Powder", Proc. of Respiratory Drug Delivery V (5), Phoenix, AZ, Apr. 1996 pp. 1–12.

Dr. Brian H. Kaye, "Sampling and Characterization Research: Developing Two Tools for Power Testing", Powder and Bulk Engineering, vol. 10, No. 2, Feb. 1996, 6 pages.

Dr. Brian H. Kaye, "Monitoring Mixture Structure by Size Characteristics of the Ingred.", Proc. Of partec '95, 6th European Symp. On Particle Char., Nuremberg, Mar. 21–23, 1996, pp. 421–426.

Dr. Brian H. Kaye, "The Effect of Flowagents on the Rheology of a Plastic Powder", Particle and Particle Systems Characterization, vol. 12, (1995), pp. 194–197.

Dr. Brian H. Kay et al, "Studying the Avalanching Behavior of a Powder in a Rotation Disc", Particle and Particle Systems Characteristics, vol. 12, (1995) pp. 232–236.

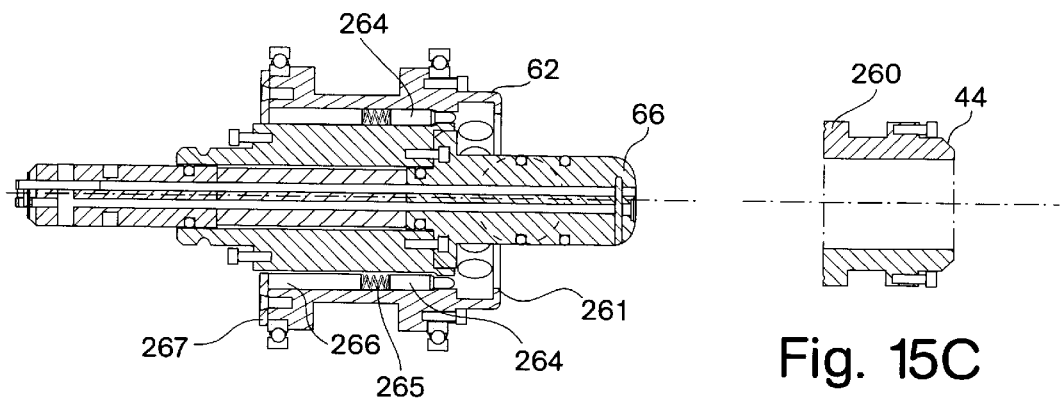
Fig. 15A
Fig. 15C
Fig. 15B
Fig. 15D

APPARATUS FOR DETERMINING POWDER FLOWABILITY

FIELD OF THE INVENTION

This invention relates to apparatus for processing and characterizing powder samples and, more particularly, to apparatus for determining powder flowability by sensing powder avalanching within a rotating sample drum. The apparatus may include a gas conditioning system for controlling and measuring the gas environment within the sample drum. The apparatus may also include a vibration mechanism for vibrating the sample drum.

BACKGROUND OF THE INVENTION

Powders composed of coarse and fine particles are utilized in many industrial processes. Examples of powders include foods, pharmaceuticals, abrasives, pigments, plastics, magnetic coating materials and the like. The particles may range in diameter from less than 1 micrometer to 1000 micrometers or more. In the industrial processing of powders, it is useful to characterize the physical properties of the powders being processed. Important powder properties include particle size distribution, particle cohesiveness and powder flowability. A particle sizing system for particle size measurement utilizing a time-of-flight technique is disclosed in U.S. Pat. No. 4,895,034, issued Jan. 23, 1990 to Poole. A system for dispersing dry particles in a gas stream for measurement is disclosed in U.S. application Ser. No. 08/204,476, filed Mar. 1, 1994 and assigned to the assignee of the subject application.

Powder flowability is an important characteristic in processes which involve the transporting of powders. Examples of such processes include flow of powders into molds, flow of powders through pneumatic systems and flow of powders to and from containers, such as trucks. The flowability may affect the energy required to transport the powder. Furthermore, powders which have poor flowability characteristics may cause blockages in powder transport systems. Powder flowability depends on powder type, particle size, moisture content and the presence of impurities. A powder with high moisture content may have very different flowability from the same powder with low moisture content.

One prior art technique for determining flowability involves passing the powder being characterized through a device similar to an hourglass. The powder passing through the device forms a peak having an angle of repose with respect to horizontal. The angle of repose is the maximum angle which may be present in a powder sample and is a measure of powder flowability.

A system for characterizing powder avalanche in a rotating drum is disclosed by B. H. Kaye in *Powder and Bulk Engineering*, Feb., 1996. In the disclosed system, a light beam is directed through a transparent, rotating drum containing a powder sample. As the drum rotates, the powder avalanches at periodic intervals. A photocell array positioned on the opposite side of the drum is blocked to a greater or lesser degree as the powder avalanches within the drum. The output of the photocell array represents powder avalanching within the drum. While the disclosed system provides generally satisfactory results, particles of the powder sample may stick to the walls of the sample drum, thus giving an erroneous indication of avalanching.

SUMMARY OF THE INVENTION

According to a first aspect of the invention, apparatus for determining flowability of a powder by sensing powder avalanching is provided. The apparatus comprises a sample drum having a generally cylindrical sample chamber for holding a power sample, a support frame including a drum shaft for supporting the sample drum for rotation, a drive motor and a drive mechanism coupled between the drive motor and the drum shaft such that the drum rotates when the drive motor is energized. The apparatus further comprises a backlash sensor for sensing intermittent reverse angular displacement of the drum caused by avalanching of the powder sample within the sample chamber as the drum rotates and for producing in response thereto an electrical signal that is representative of the avalanching of the powder sample.

The backlash sensor may comprise a stationary member that is fixed with respect to the support frame, a slip ring assembly frictionally coupled to the drive shaft such that the slip ring assembly rotates with the drive shaft except when the slip ring assembly contacts the stationary member, and a device for sensing reverse angular displacement of the slip ring assembly with respect to the stationary member. In a first embodiment, the device for sensing reverse angular displacement may comprise a pair of electrical contacts which open in response to reverse angular displacement of the slip ring assembly with respect to the stationary member. In a second embodiment, the device for sensing reverse angular displacement may comprise an optical sensor which optically senses reverse angular displacement of the slip ring assembly and provides an electrical signal in response thereto. In a third embodiment, the device for sensing reverse angular displacement may comprise a magnetic element attached to the slip ring assembly and a Hall effect sensor attached to the stationary member. The Hall effect sensor senses reverse angular displacement of the slip ring assembly and provides an electrical signal in response thereto.

In another embodiment, the backlash sensor may comprise an optical encoder attached to the drum shaft. The output signal of the optical encoder changes phase in response to avalanching of the powder sample within the sample chamber.

According to a feature of the invention, the apparatus may include a protractor coupled to the sample drum. The protractor is used for measuring an angle of repose of the powder sample within the sample drum.

According to another feature of the invention, the apparatus may include a gas conditioning system for controllably circulating a gas through the sample chamber. The gas conditioning system may include a humidity sensor for sensing the humidity level and/or a temperature sensor for sensing the temperature of the gas in the sample chamber. The gas conditioning system may further include means for controlling the humidity and/or the temperature of the gas in the sample chamber.

According to a further feature of the invention, the apparatus may include a vibration mechanism including a vibration motor coupled to the sample drum for vibrating the sample drum when the vibration motor is energized. The drive motor and the vibration motor may be energized at different times or may be energized simultaneously.

According to another aspect of the invention, apparatus for determining flowability of a powder by sensing powder avalanching is provided. The apparatus comprises a sample drum having a generally cylindrical sample chamber for holding a powder sample, a support frame including a drum shaft for supporting the drum for rotation, a drive motor, and a drive mechanism coupled between the drive motor and the drum shaft such that the sample drum rotates when the drive motor is energized. The apparatus further comprises a torque loading sensor for sensing variations in torque loading in the drive mechanism caused by avalanching of the powder sample and for sensing powder sample position within the sample chamber as the drum rotates and for producing in response thereto an electrical signal that is representative of the powder sample position and the avalanching of the powder sample. The drive mechanism may comprise first and second pulleys respectively mounted on the drive motor and the drum shaft, and a drive belt connected between the first and second pulleys. The torque loading sensor may comprise a load cell for sensing tension in the drive belt.

According to a further aspect of the invention, apparatus for processing a powder is provided. The apparatus comprises a sample drum having a generally cylindrical sample chamber for holding a powder sample, a support frame including a drum shaft for supporting the drum for rotation, a drive motor and a drive mechanism coupled between the drive motor and the drum shaft such that the sample drum rotates when the drive motor is energized. The apparatus further comprises interengaging coupling elements on the drum shaft and the sample drum which permit the drum to be easily locked in position on the drum shaft and to be easily unlocked and removed from the drum shaft.

According to a further aspect of the invention, apparatus for characterizing a powder is provided. The apparatus comprises a sample drum having a generally cylindrical sample chamber for holding a powder sample, a support frame including a drum shaft for supporting the drum for rotation, a drive motor, and a drive mechanism coupled between the drive motor and the drum shaft such that the sample drum rotates when the drive motor is energized. The apparatus further comprises an energy beam scanner for directing an energy beam radially outwardly from the central axis of the sample chamber and for sensing a reflected energy beam, and a scanner for rotating the energy beam about the central axis relative to the drum. The energy beam scanner provides an electrical signal representative of a surface contour of the powder sample in response to the reflected energy beam. The energy beam may, for example, comprise a light beam or an ultrasonic beam.

According to still another aspect of the invention, apparatus for processing powder is provided. The apparatus comprises a sample drum having a generally cylindrical sample chamber for holding a powder sample, a support frame including a drum shaft for supporting the drum for rotation, a drive motor and a drive mechanism coupled between the drive motor and the drum shaft such that the sample drum rotates when the drive motor is energized. The apparatus further comprises a vibration mechanism including a vibration motor coupled to the sample drum for vibrating the drum when the vibration motor is energized. The drive motor and the vibration motor may be energized at different times or may be energized simultaneously.

BRIEF DESCRIPTION OF THE DRAWINGS

For a better understanding of the present invention, reference is made to the accompanying drawings, which are incorporated herein by reference and in which:

FIGS. 15A–15D are details showing the interengaging elements on the hub rotor and the sample drum hub.

DETAILED DESCRIPTION

Figure 1:
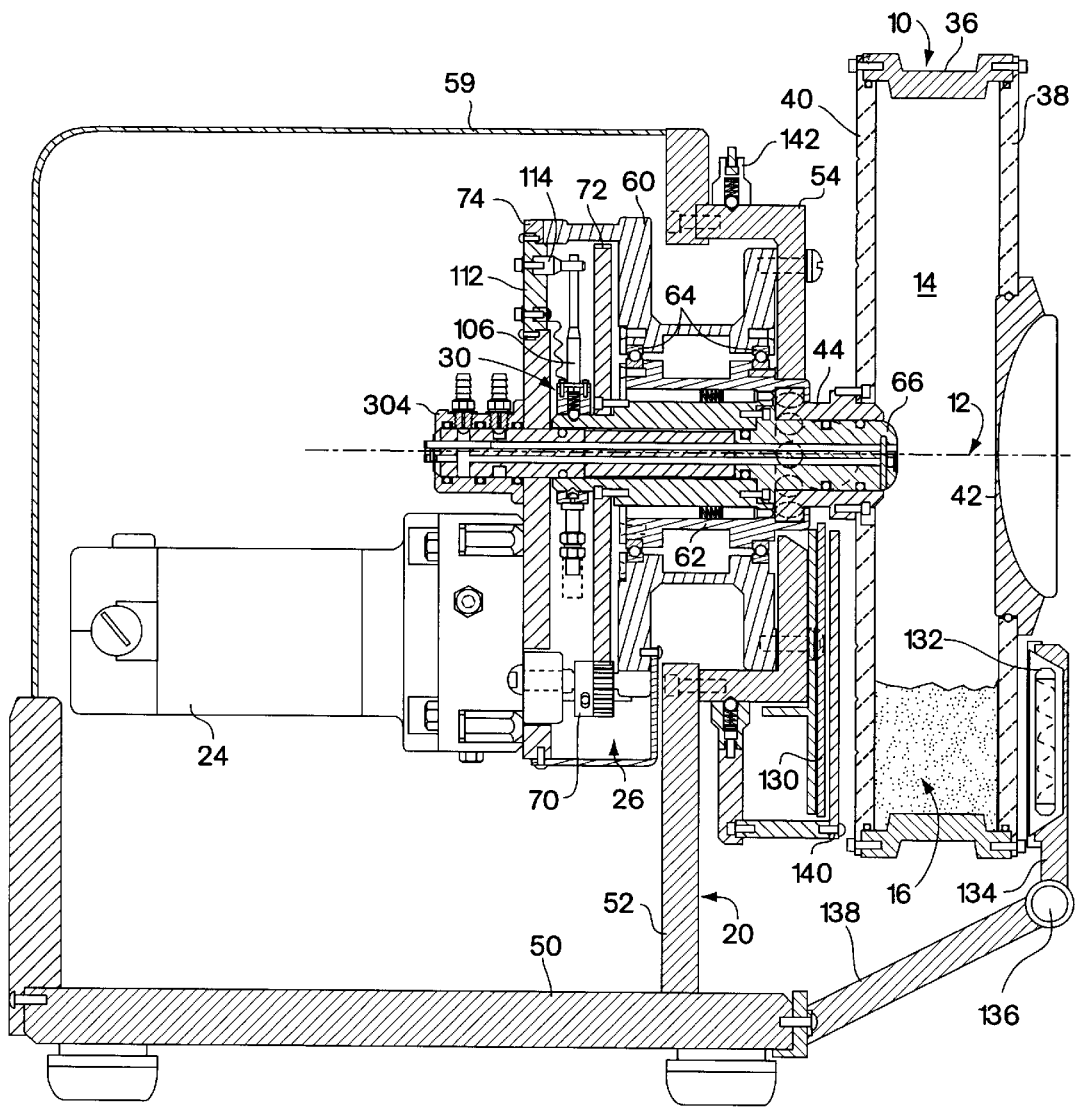
FIG. 1 is a cross-sectional view of apparatus for determining flowability of a powder in accordance with the present invention.
Figure 2:
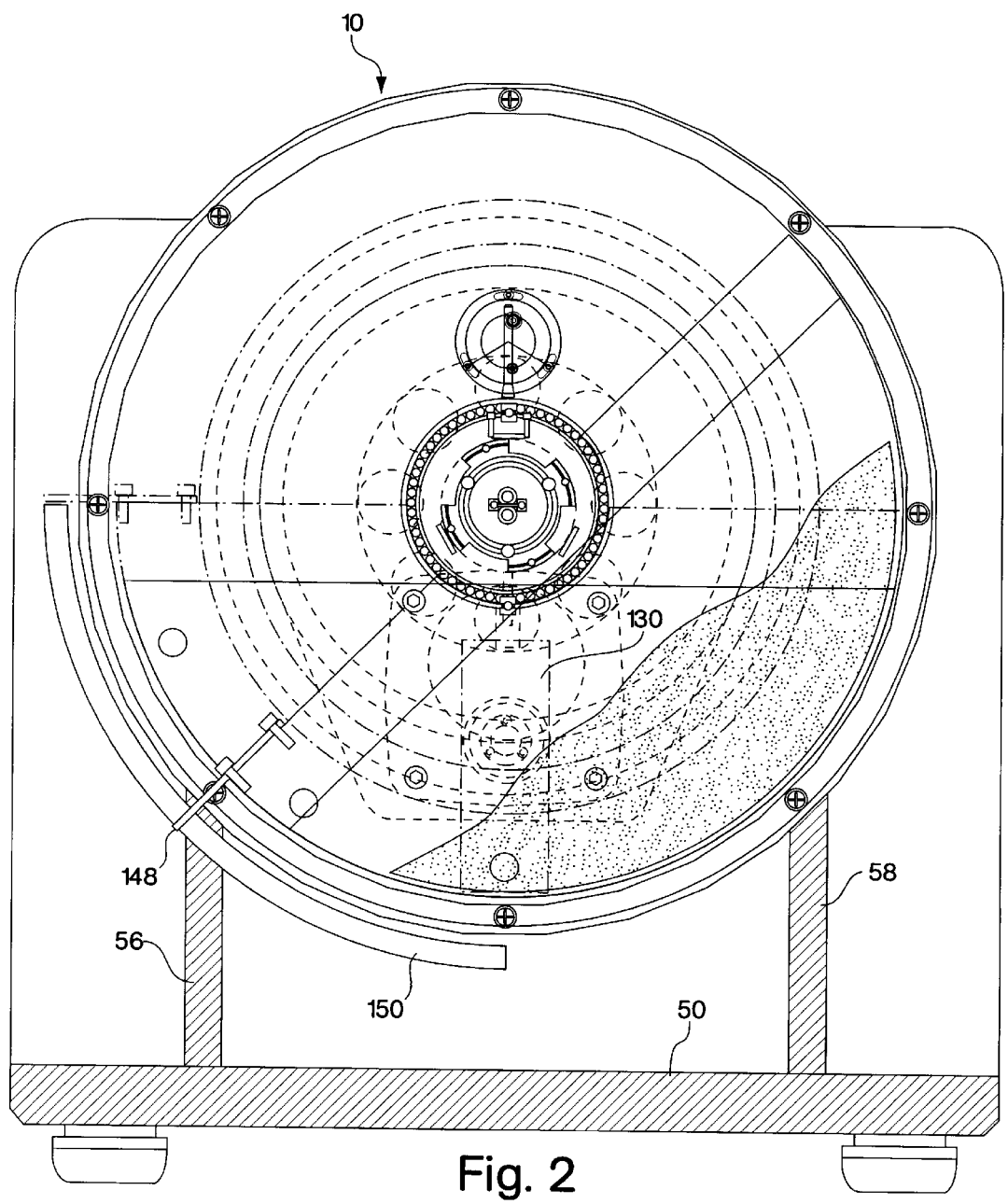
FIG. 2 is a front view of the apparatus of FIG. 1.
Figure 3:
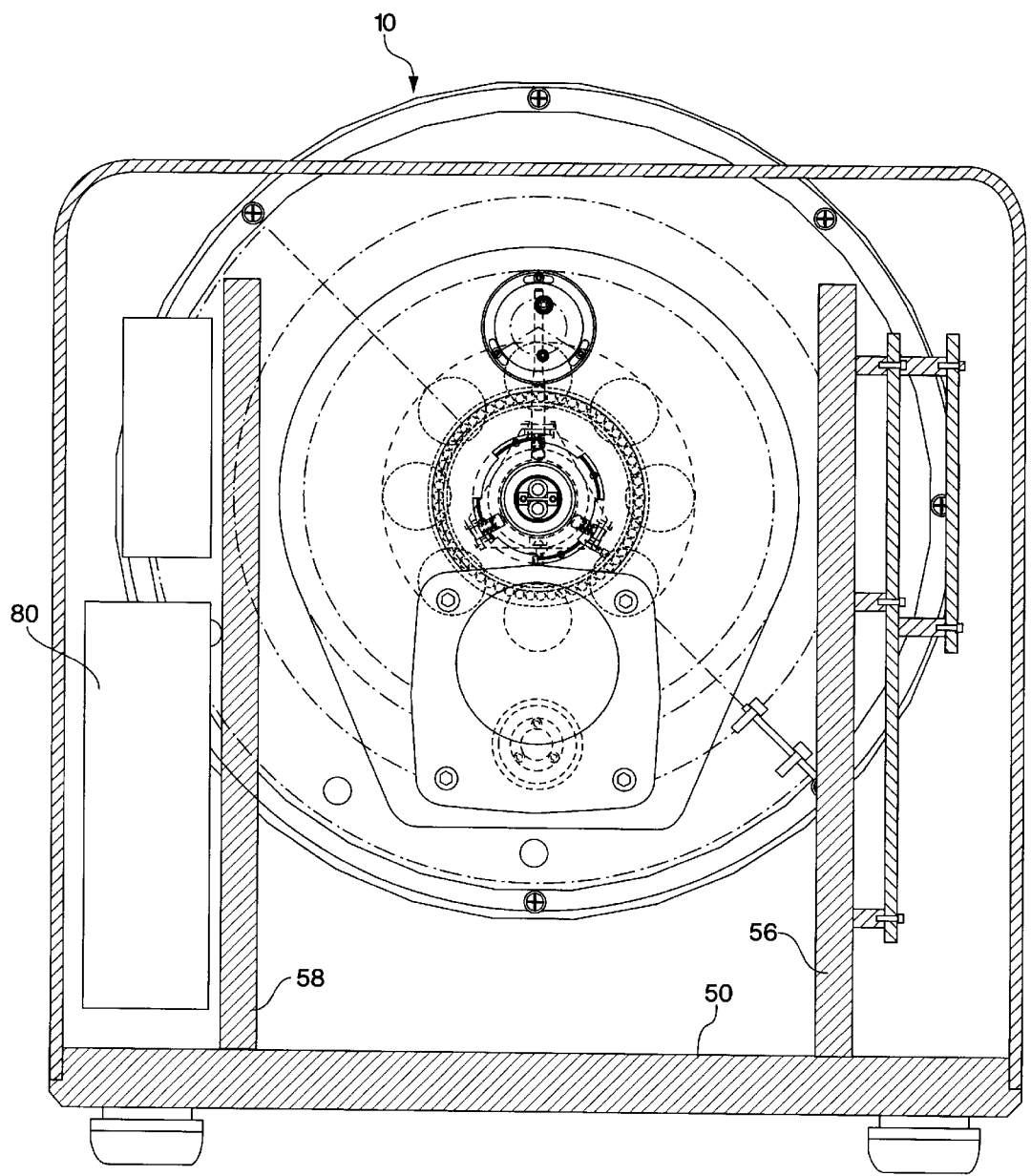
FIG. 3 is a rear view of the apparatus of FIG. 1.

Apparatus for determining powder flowability in accordance with a first embodiment of the invention is shown in FIGS. 1–3. The apparatus includes a sample drum 10 having a central axis 12 and a generally cylindrical sample chamber 14 for holding a powder sample 16. The apparatus further comprises a support frame 20 for supporting the sample drum 10 for rotation about central axis 12, a drive motor 24 and a drive mechanism 26 coupled between drive motor 24 and sample drum 10, such that the sample drum 10 rotates about central axis 12 when the drive motor 24 is energized. The apparatus further comprises an avalanche sensor 30 for sensing avalanching of the powder sample within the sample chamber 14. As the sample drum 10 rotates, the avalanche sensor 30 produces an electrical signal that is representative of the avalanching of the powder sample.

The sample drum 10 may include a generally cylindrical rim 36, transparent sidewalls 38 and 40, an access cover 42 and a sample drum hub 44. The support frame 20 may include a baseplate 50, a main support plate 52 secured to baseplate 50, and a motor mounting cap 54 secured to main support plate 52. Outriggers 56 and 58 secured between baseplate 50 and main support plate 52 stabilize the main support plate 52. As best shown in FIG. 3, electronic circuit boards and/or modules, such as module 80, may be mounted to outriggers 56 and 58. A gas conditioning system, as described below, may also be mounted to the outriggers.

A hub stator 60 is mounted to cap 54, and a hub rotor 62 is rotatably mounted within hub stator 60 by bearings 64. Secured axially within hub rotor 62 is a hub mandrel 66. The hub rotor 62 and the sample drum hub 44 include interengaging locking elements which lock the sample drum 10 to hub rotor 62 and which permit the sample drum 10 to be unlocked and removed from the hub rotor 62. As described below, the hub mandrel 66 may be provided with passages for circulation of a gas through the sample chamber 14 during rotation of sample drum 10. The drive motor 24 is mounted to a motor mounting plate 74 which in turn is secured to hub stator 60. The drive mechanism 26 may include a pinion gear 70 attached to the drive shaft of motor 24 and a gear 72 secured to hub rotor 62. In a preferred embodiment, the drive motor 24 comprises a gear headed, variable speed, brush or brushless DC motor such as, for example, a 24 volt DC instrument motor, type 24 A4BEPM-D3, Model 4690 sold by Bodine Electric Company, and the drive mechanism 26 is designed to provide rotation of sample drum 10 at a rate of about 0.1–2 rpm for sample drum applications and higher speed for mixing chamber applications. A cover 59 encloses drive motor 24 and drive mechanism 26.

Figure 4:
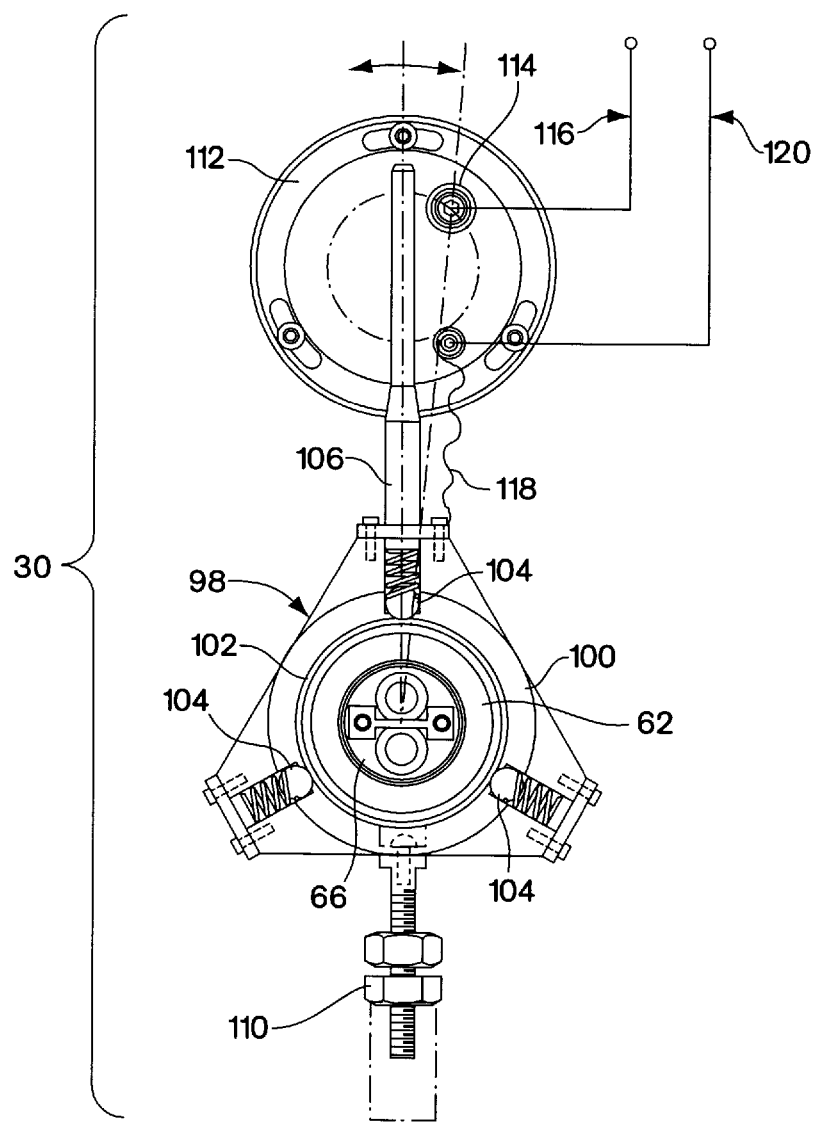
FIG. 4 is a detail of the powder avalanche sensor in the apparatus of FIG. 1.

A detail of avalanche sensor 30, as viewed along axis 12, is shown in FIG. 4. The avalanche sensor 30 is based on sensing backlash, or reverse angular displacement, of the sample drum 10 when the powder sample in sample drum 14 avalanches. In particular, assuming some friction between particles in the powder sample, the powder sample tends to rotate upwardly at the periphery of the sample chamber as the sample drum rotates. At some point, gravitational force overcomes the friction between particles and the powder sample avalanches downwardly toward the lower portion of the sample chamber. The avalanching of the powder sample produces a backlash, or reverse angular displacement, of the sample drum. This process is repeated as the sample drum rotates. The avalanching characteristics of the powder sample depend on its flowability.

Referring again to FIG. 4, the avalanche sensor 30 comprises a slip ring assembly 98 including a slip ring 100 having a central opening 102 for receiving hub rotor 62 and hub mandrel 66. The slip ring 100 is provided with three equally spaced radial bores. A spring-loaded ball 104 of a non-stick material, such as Teflon, is mounted in each radial bore. A conductive rod 106 extends radially from slip ring 100. The spring-loaded balls 104 are in frictional contact with hub rotor 62. The frictional force is adjusted such that slip ring assembly 98 rotates with hub rotor 62, except when rod 106 contacts a stationary member, such as post 114. Then, hub rotor 62 rotates within slip ring assembly 98. A counterweight 110 may be connected to slip ring 100. The slip ring assembly 98 includes slip ring 100, spring-loaded balls 104, rod 106 and counterweight 110.

A plate 112 is secured to motor mounting plate 74 (see FIG. 1). Post 114 extends from plate 112 and is positioned to intercept rod 106. Post 114 is an electrically conductive material and is connected via electrical leads 116 to an electrical circuit. Similarly, rod 106 is connected via electrical leads 118 and 120 to the electrical circuit. When rod 106 is physically in contact with post 114, the electrical circuit between leads 116 and 120 is completed. When rod 106 is spaced from post 114, the electrical circuit is open. Thus, rod 106 and post 114 function as an electrical switch. The counterweight 110 may be used to adjust the characteristics of the contact opening and closing.

In operation, the hub rotor 62 rotates in a clockwise direction as the sample drum 10 rotates. Frictional contact between the spring-loaded balls 104 and hub rotor 62 causes the slip ring 100 to rotate in a clockwise direction until rod 106 contacts post 114, thereby closing the electrical circuit between leads 116 and 120. In the absence of a powder sample in sample drum 10, rod 106 and post 114 remain in contact as the sample drum 10 rotates. When a powder sample is present in sample chamber 14, the powder avalanches intermittently as the sample drum rotates. Each time the powder sample avalanches, the sample drum 10, the hub mandrel 66 and the hub rotor 62 are subjected to backlash, or reverse angular displacement, in a counterclockwise direction in FIG. 4. Because of the frictional contact between balls 104 and hub rotor 62, the backlash causes slip ring 100 and rod 106 to be displaced in a counterclockwise direction, and contact between rod 106 and post 114 is broken. As a result, the electrical circuit between leads 116 and 120 is opened. Shortly thereafter, continued drum rotation brings rod 106 back into contact with post 114, and the electrical circuit is again completed. The contact between rod 106 and post 114 is broken each time the powder sample avalanches within sample chamber 14, thus producing a more or less continuous train of switch closures. When a voltage is applied between leads 116 and 120, the resulting waveform is a series of pulses. The widths of the pulses and the times between pulses are representative of the characteristics of the powder sample avalanching. The characteristics of the powder sample avalanching, in turn, are representative of the flowability of the powder. The avalanche sensor shown in FIG. 4 and described above provides a low cost approach to powder avalanche sensing.

Additional features of the apparatus are described with reference to FIGS. 1–3. A solar cell array 130 may be mounted to cap 54 adjacent to the lower portion of sample drum 10. A lamp 132 is mounted on the opposite side of sample drum 10 from solar cell array 130. The lamp 132 is mounted on a swing-out arm 134 to provide clearance for installation and removal of sample drum 10. The swing-out arm 134 is connected via a hinge 136 and a bracket 138 to baseplate 50. The lamp 132 may, for example, be a DC filament lamp. A lamp intensity control (not shown) may be provided. The variation in coverage of the solar cell array by the powder sample as the sample drum rotates is an indication of avalanching within the sample chamber 14. The output electrical signal from the solar cell array thus represents powder avalanching.

The apparatus may also be provided with a protractor 140 for measuring the angle of repose of the powder sample within sample drum 10. The protractor 140 is rotatably mounted to cap 54 via a ring 142. The protractor 140 is rotated into alignment with the surface of the powder sample in sample drum 10. The protractor 140 includes grating lines which may be aligned with the surface of the powder sample. The protractor 140 further includes a pointer 148 which passes over a fixed scale 150. The scale reading indicates the angle of repose.

Figure 5:
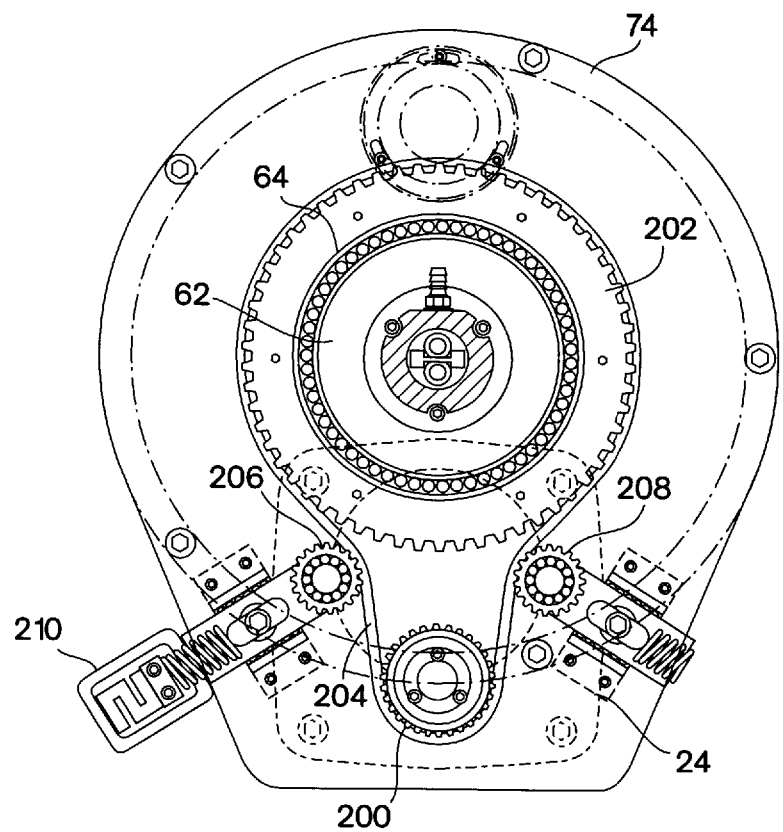
FIG. 5 is a detail of another embodiment of a powder avalanche sensor in accordance with the invention.

Another embodiment of an avalanche sensor is shown in FIG. 5. A partial rear view of the apparatus along axis 12 with the cover 59 removed is shown in FIG. 5. Like elements in FIGS. 1–3 and 5 have the same reference numerals. A first pulley 200 is attached to the shaft of drive motor 24, and a second pulley 202 is attached to hub rotor 62. A drive belt 204 is connected between pulleys 200 and 202. Idler pulleys 206 and 208 are symmetrically positioned to bear against drive belt 204. Idler pulley 206 is mechanically coupled to a load cell 210 which senses drive belt tension.

As the sample drum 10 rotates and the powder sample intermittently avalanches within the sample chamber, the torque applied to the sample drum by the drive motor 24 varies. The torque variation is sensed by load cell 210. The load cell provides an electrical signal that is representative of the drive belt tension. The waveform of the electrical signal is representative of torque variations and is therefore representative of powder avalanching within the sample chamber and is representative of powder sample position within the sample chamber. As the powder sample is elevated to a higher position within the sample drum, the torque load on the drive mechanism increases. The load cell 210 supplies an analog output waveform which provides more information regarding the characteristics of the powder sample than avalanche sensors which supply binary output waveforms.

Figure 6:
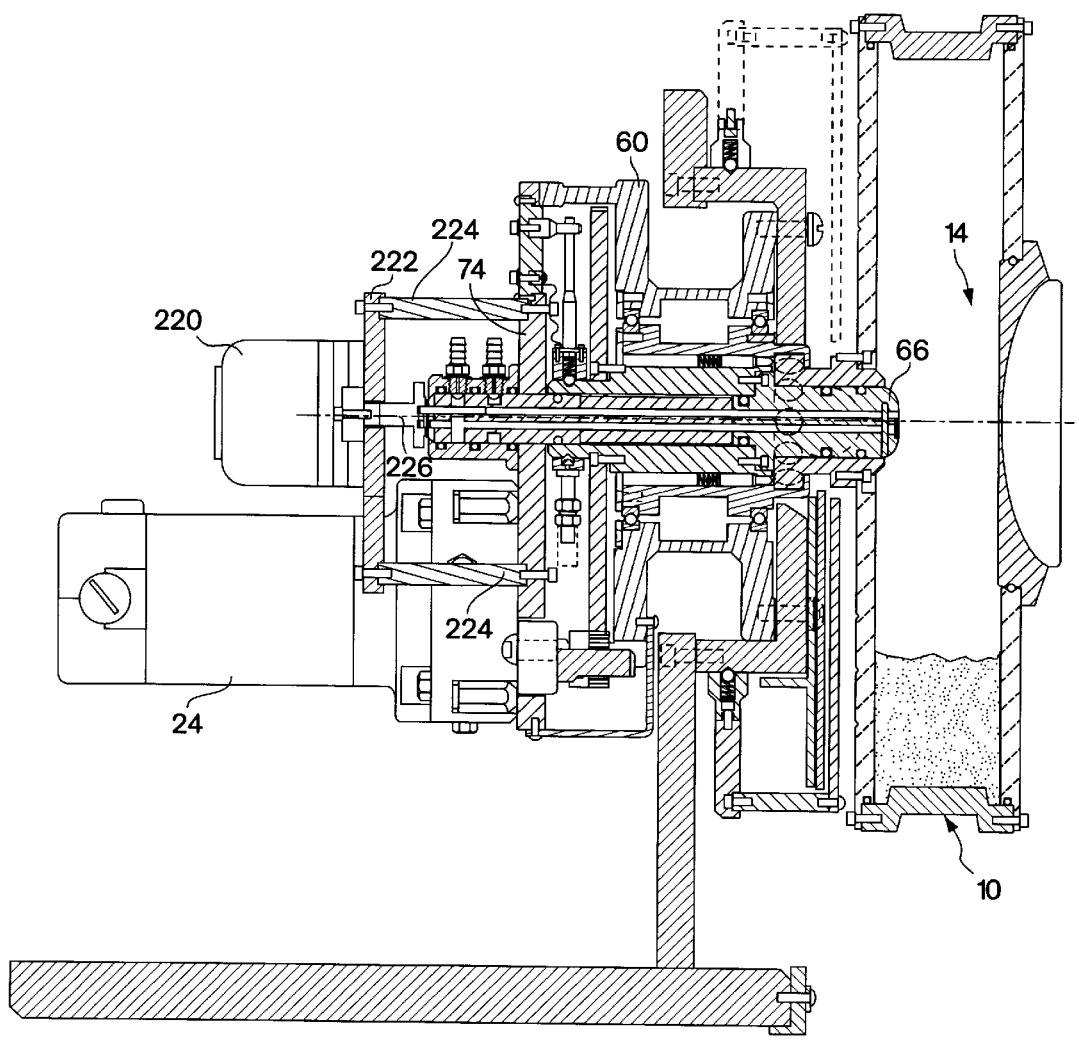
FIG. 6 is a partial cross-sectional view of apparatus for determining powder flowability using a shaft encoder for sensing powder avalanche.

A further embodiment of an avalanche sensor for sensing powder avalanching within sample drum 10 is shown in FIG. 6. Like elements in FIGS. 1–3 and 6 have the same reference numerals. A shaft encoder 220 is operationally connected to hub mandrel 66. In particular, shaft encoder 220 is mounted to a plate 222 which is spaced from motor mounting plate 74 by spacers 224. A shaft 226 of encoder 220 is connected to hub mandrel 66 so that the shaft encoder 220 senses rotation of sample drum 10. As known in the art, a shaft encoder produces a predetermined number of pulses for each rotation of its shaft. Avalanching of the powder sample within sample chamber 14 and the resulting backlash of sample drum 10 cause a phase shift in the output signal of shaft encoder 220. The magnitude and duration of the phase shift are representative of the powder avalanche characteristics.

Figure 7:
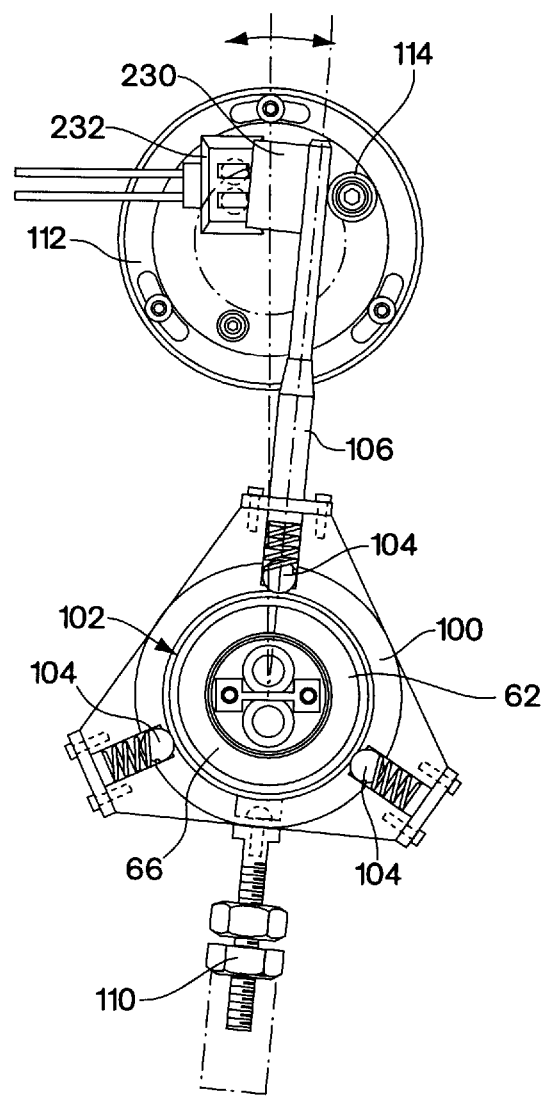
FIG. 7 is a detail of still another embodiment of a powder avalanche sensor in accordance with the invention.

Yet another embodiment of an avalanche sensor is shown in FIG. 7. Like elements in FIGS. 4 and 7 have the same reference numerals. The sensor of FIG. 7 is similar to the sensor of FIG. 4 and relies upon sensing backlash of the sample drum 10 produced by powder avalanching. The sensor of FIG. 7 includes slip ring 100 having spring-loaded balls 104 which frictionally bear against hub rotor 62. In the embodiment of FIG. 7, the rod 106 is not necessarily conductive. The sensor of FIG. 7 relies upon optical rather than electrical sensing. A shutter 230 is attached to the upper end of rod 106. An optical sensor 232 is positioned to sense the presence or absence of shutter 230. In the position shown in FIG. 7 where rod 106 is in contact with post 114, representing rotation of the sample drum without avalanching, the optical sensor 232 does not sense shutter 230. Upon avalanching of the powder sample, sample drum backlash angularly displaces rod 106 in a counterclockwise direction, thereby bringing shutter 230 into proximity to optical sensor 232 and changing the output state of optical sensor 232. The output electrical signal of optical sensor 232 is representative of powder avalanching characteristics in the same manner as the sensor 30 shown in FIG. 4 and described above. The optical sensor 232 may be of the reflective type, wherein the presence of shutter 230 is determined from a light beam transmitted by the optical sensor 232 and reflected from the surface of shutter 230. In an alternative configuration, an optical transmitter and an optical receiver are spaced apart, and a light beam is transmitted from the transmitter to the receiver. The light beam is broken when the shutter 230 rotates into the light beam path, thereby producing an output signal from the receiver. Other optical sensing techniques may be used within the scope of the present invention. Optical sensor devices and techniques are well known to those skilled in the art.

Figure 14:
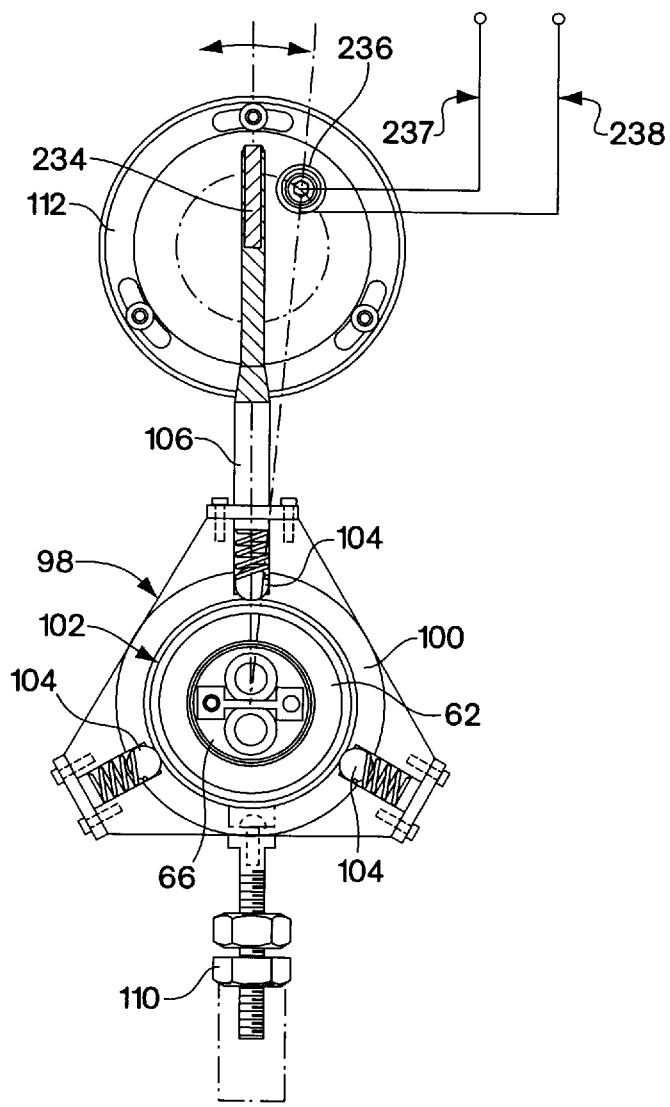
FIG. 14 is a detail of yet another embodiment of a powder avalanche sensor in accordance with the invention.

A further embodiment of an avalanche sensor is shown in FIG. 14. Like elements in FIGS. 4 and 14 have the same reference numerals. The sensor of FIG. 14 is similar to the sensor of FIG. 4 and relies upon sensing the backlash of the sample drum 10 produced by powder avalanching. The sensor of FIG. 14 includes slip ring 100 having spring-loaded balls 104 which frictionally bear against hub rotor 62. In the embodiment of FIG. 14, the rod 106 is not necessarily conductive. The sensor of FIG. 14 relies upon Hall effect sensing rather than electrical sensing. A magnetic ferrite core insert 234 is attached to the upper end of rod 106. A Hall effect sensor 236 is mounted to plate 112 and is positioned to contact magnetic ferrite core insert 234 when the rod 106 is rotated by hub rotor 62. The Hall effect sensor 236 includes a magnetically activated switch and a transistor amplifier which provide an output signal on leads 237 and 238. The output is a binary signal, depending on whether the magnetic ferrite core insert 234 is within effective proximity triggering distance to the Hall effect sensor 236. The magnetic ferrite core insert 34 is normally within effective proximity triggering distance to the Hall effect sensor 236 during rotation of the sample drum. Upon avalanching of the powder sample, sample drum backlash angularly displaces rod 106 in a counterclockwise direction, thereby changing the output state of Hall effect sensor 236. The output electrical signal of Hall effect sensor 236 is representative of powder avalanching characteristics in the sample drum. The Hall effect sensor has an advantage that the triggering of the backlash event can be electronically tuned.

Figure 8:
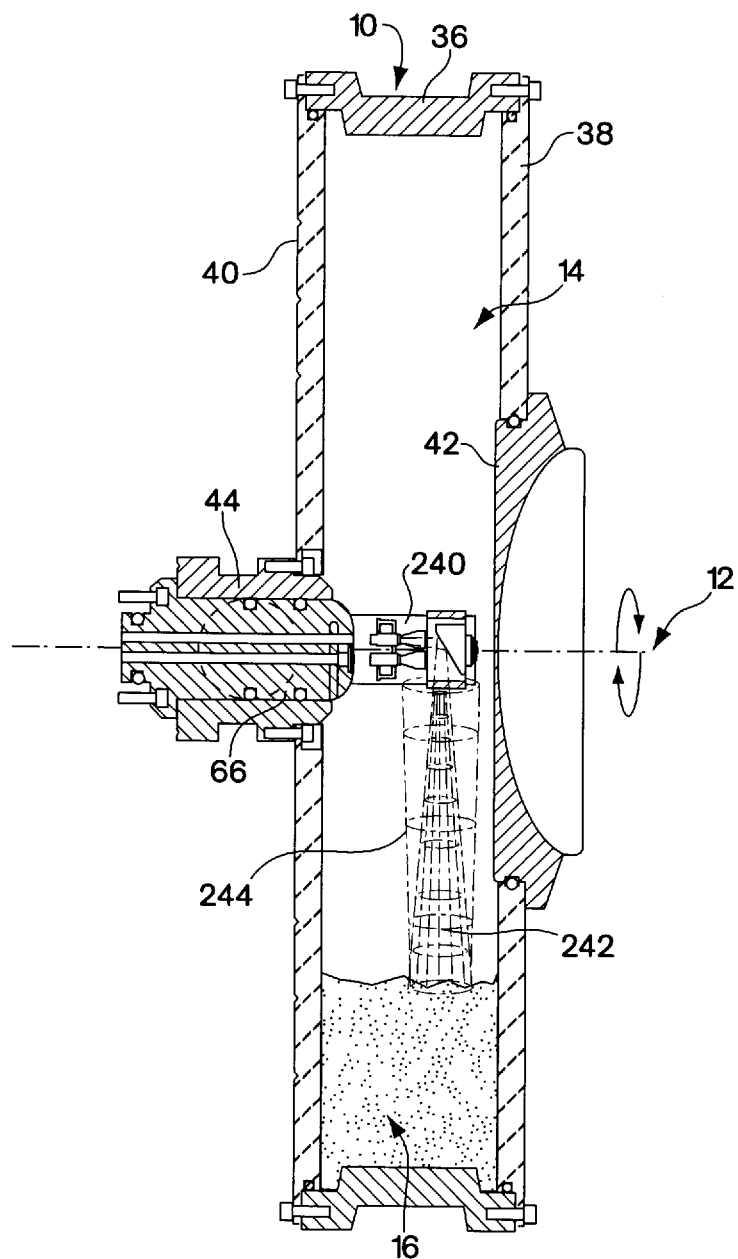
FIG. 8 is a cross-sectional view of a sample drum showing an energy beam scanner for mapping the surface contour of the powder in the drum.
Figure 9:
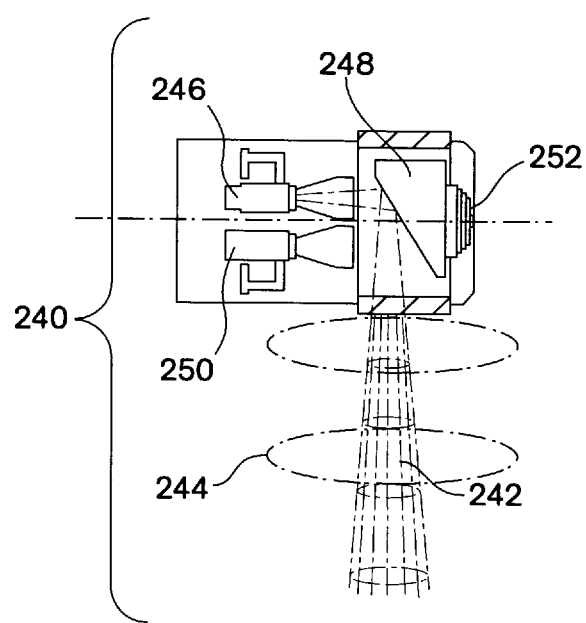
FIG. 9 is a detail of the energy beam scanner shown in FIG. 8.

Still another embodiment of an avalanche sensor is shown in FIGS. 8 and 9. Like elements in FIGS. 1, 8 and 9 have the same reference numerals. In the embodiment of FIGS. 8 and 9, an energy beam scanner 240 is mounted to hub mandrel 66 within sample chamber 14. The energy beam scanner 240 is located on the central axis 12 of sample drum 10 and directs an energy beam 242 radially outwardly toward the rim 36 of sample drum 10. The energy beam 242 may, for example, be a light beam, an ultrasonic beam or any other suitable beam. A portion of the energy beam 242 is reflected by the powder sample or by rim 36 to form a reflected beam 244. The reflected beam 244 is sensed by the energy beam scanner 240. The energy beam 242 is rotated, or scanned, about axis 12 faster than the speed of rotation of sample drum 10. As a result, the reflected beam 244 represents the surface contour of the powder sample within sample chamber 14 as a function of time.

An example of a suitable energy beam scanner 240 is shown in FIG. 9. A light source 246 directs a light beam along axis 12 at a mirror 248 having a reflective surface disposed at 45° with respect to axis 12. An optical sensor 250 senses the reflected light beam, which is also reflected by mirror 248. A motor 252 rotates mirror 248 about axis 12 to effect scanning of the energy beam 242.

By mapping the surface contour of the powder sample, the energy beam scanner 240 senses powder avalanching within the sample chamber 14. The surface contour changes as powder avalanching occurs. The energy beam scanner 240 may obtain additional information regarding powder characteristics that is not available by sensing backlash or torque variation as described above. For example, the energy beam scanner 240 may determine whether the avalanching of the powder sample is a bulk effect or a surface effect.

The sample drum hub 44 and the hub rotor 62 preferably have interengaging locking elements which permit different sample drums to easily be locked into place on the apparatus and to easily be unlocked and removed from the apparatus. FIG. 15A is a cross-sectional view of the hub rotor 62, hub mandrel 66 and related elements. FIG. 15B is an end view of the hub rotor 62, hub mandrel 66 and related elements. FIG. 15C is a cross-sectional view of sample drum hub 44, and FIG. 15D is an end view of sample drum hub 44. As shown in FIGS. 15A–15D, the sample drum hub 44 may include four outwardly extending tabs 260 and the hub rotor 62 may include four inwardly extending tabs 261 which define notches 262 between them. Each of the tabs 260 is provided with detents. In order to install the sample drum on the apparatus, the tabs 260 are aligned with notches 262. The sample drum is pushed inwardly and is rotated until spring-loaded pins 264 in hub rotor 62 interlock with the detents 263 in tabs 260. A groove 269 in each tab 260 guides pin 264 to detent 263. The process is reversed to remove the sample drum from the apparatus and can be accomplished by rotating in either the clockwise or counterclockwise direction.

Figure 10:
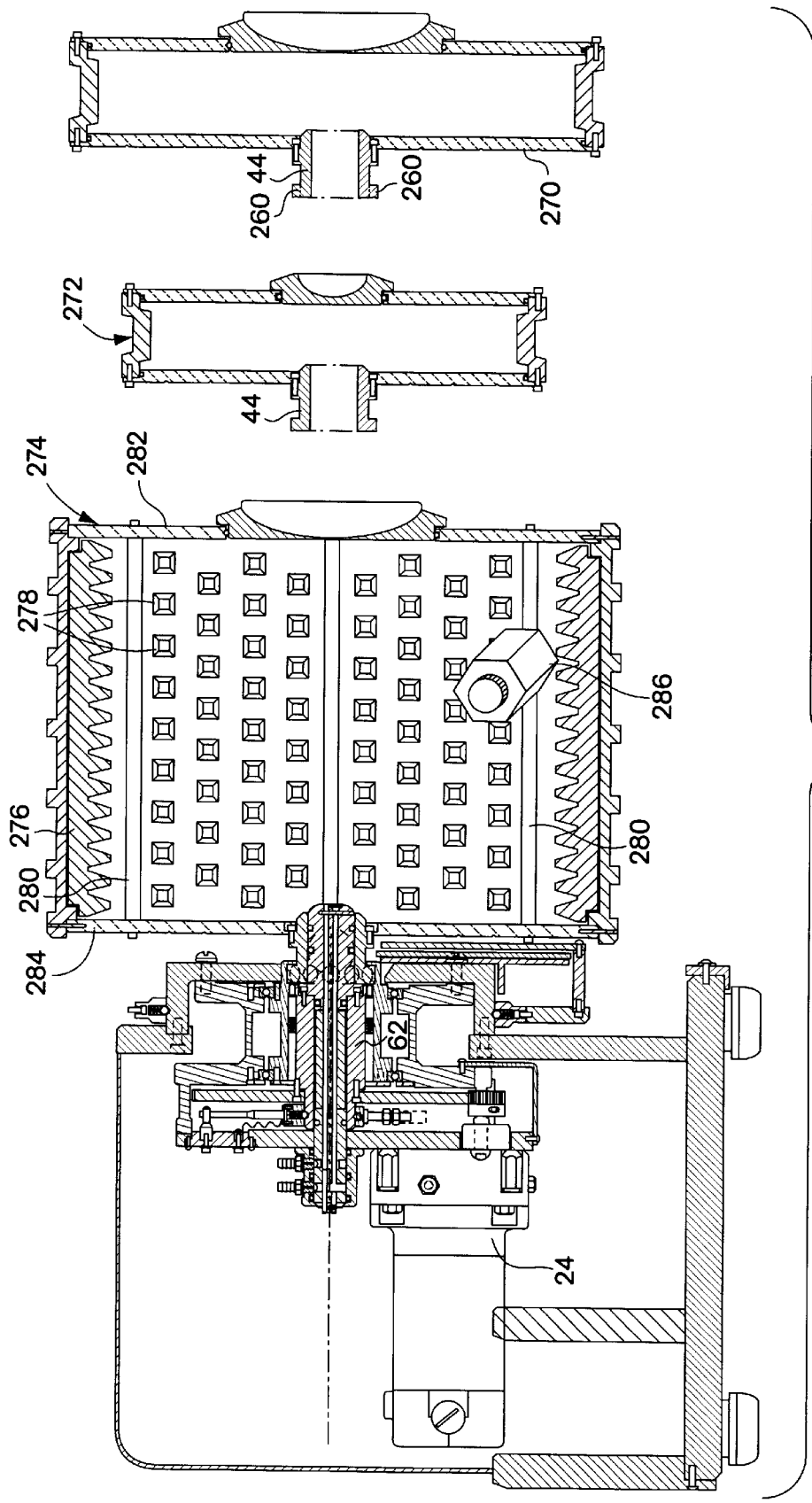
FIG. 10 is a pictorial diagram that illustrates the use of interchangeable sample drums in the apparatus of FIG. 1.

A further aspect of the invention is illustrated in FIG. 10. Like elements in FIGS. 1–3 and 10 have the same reference numerals. The interchangeability of sample drums in the apparatus is illustrated in FIG. 10. Three different sample drums are shown. A large sample drum 270, which corresponds sample drum 10 shown in FIGS. 1–3, and a small sample drum 272 differ primarily in powder sample capacity. A mixing drum 274 performs mixing of powder samples as described in the aforementioned article by B. H. Kaye in *Powder and Bulk Engineering*. The mixing drum 274 has an axial dimension that is approximately equal to its diameter. A foam liner 276 having multiple inward projections 278 is located on the inside cylindrical wall of mixing drum 274. Reinforcing rods 280 are secured between sidewalls 282 and 284 of the mixing drum 274. A sample container 286, such as a small jar having a powder sample therein, is placed in the mixing drum 274. As the mixing drum 274 rotates, the sample container 286 tumbles randomly within the mixing chamber. The tumbling of the sample container 286 is enhanced by the projections 278 on the wall of the chamber and by the rods 280 which, in effect, trip the sample container 286 and cause further tumbling. It will be understood that a variety of different sample drums can be installed on the apparatus.

As indicated above, spring-loaded pins 264 in hub rotor 62 interlock with detents in tabs 260 to permit easy installation and removal of sample drums. This structure also provides a safety feature. In particular, when a predetermined load is applied to the sample drum, the spring loaded pins 264 disengage from the detents in tabs 260, and the sample drum stops rotating. A further safety feature is provided by the connection between drive motor 24 and pinion gear 70. In particular, the pinion gear 70 is preferably attached to the shaft of drive motor 24 by a shear pin. When a predetermined load is applied to the sample drum 10, the shear pin is broken and rotation of the sample drum stops. Preferably, the connection between the pinion gear 70 and the shear pin is slotted so that reverse angular displacement of sample drum 10 caused by powder avalanching is not transmitted to drive motor 24.

In accordance with a further aspect of the invention, the apparatus may include a gas conditioning system for controlling and measuring the gas within the sample chamber. The characteristics of a powder sample, such as flowability, may change significantly depending on the type of ambient gas in the sample chamber, and its moisture content and temperature.

Figure 11:
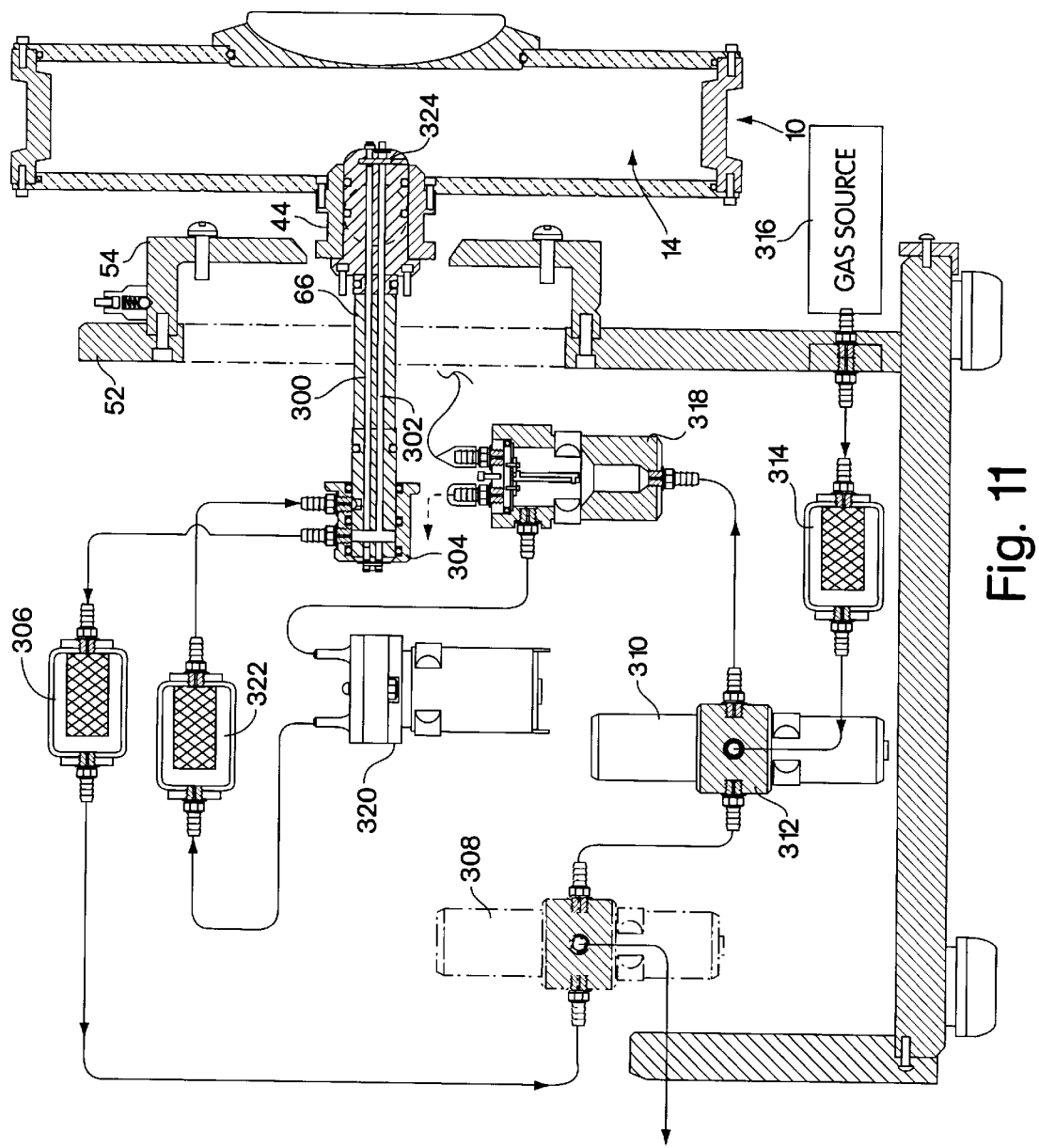
FIG. 11 is a schematic diagram showing a gas conditioning system connected to the sample chamber within a sample drum.

A block diagram of the gas conditioning system is shown in FIG. 11. As indicated above, the hub mandrel 66 includes passages for circulating a gas through the sample chamber 14. In particular, an inlet passage 302 and an outlet passage 300 extend axially through hub mandrel 66 from sample chamber 14 to a pneumatic slip ring 304 installed on hub mandrel 66. The pnematic slip ring 304 permits fixed pneumatic connections to the rotating hub mandrel 66. Inlet passage 302 is connected through a filter 306 to an optional mixing valve 308. Mixing valve 308 permits gas within the system to be exhausted to the ambient environment. One output of mixing valve 308 is connected to a mixing valve 310, which permits controlled introduction of a gas into the gas conditioning system. Inlet 312 of valve 310 is connected through a filter 314 to a gas source 316. The gas source 316 may supply ambient air, air of a predetermined moisture content and/or temperature, or a selected gas such as, for example, nitrogen. The output of mixing valve 310 is supplied to a sensor 318, which may sense humidity and/or temperature of the circulating gas. The output of sensor 318 passes through a recirculating pump 320 and a filter 322 to outlet passage 300 in hub mandrel 66. The suction port to the sample chamber 14 from inlet passage 302 preferably includes multiple tuned eduction inlets 324 to prevent disturbance of the powder sample and to minimize the amount of gas that passes directly from the discharge port 300 to the suction port of inlet passage 302. In a preferred embodiment, the components of the gas conditioning system may be mounted on a board which, in turn, is mounted on one of the outriggers 56 and 58 shown in FIG. 3.

In operation, the gas is circulated through sample chamber 14 by the gas conditioning system. The circulating gas can be measured and/or controlled. The gas conditioning system can be used in a variety of different operating modes. The humidity within the sample chamber can be measured at a fixed time or over a period of time. A decrease in humidity with time indicates that the powder sample is absorbing moisture. Conversely, an increase in humidity indicates that the powder sample is giving off moisture. The gas conditioning system can also be utilized to control the humidity level within sample chamber 14. The mixing valve 310 is pulsed so as to mix the gas circulating through the sample chamber with a gas having high or low humidity. In addition, the gas conditioning system can be utilized to circulate a gas other than air such as, for example, dry nitrogen through the sample chamber 14. The temperature of the gas may be sensed in any of the above operations.

A further aspect of the invention is described with reference to FIGS. 12 and 13. A vibration device 350, or oscillator, is attached to sample drum 10 in place of the access cover 42 shown in FIG. 1. The vibration device 350 causes vibration of the sample drum 10, either separately from rotation of sample drum 10 or simultaneously with rotation. Vibration of the sample drum 10 may be useful, for example, for mixing of the powder sample.

Figure 12:
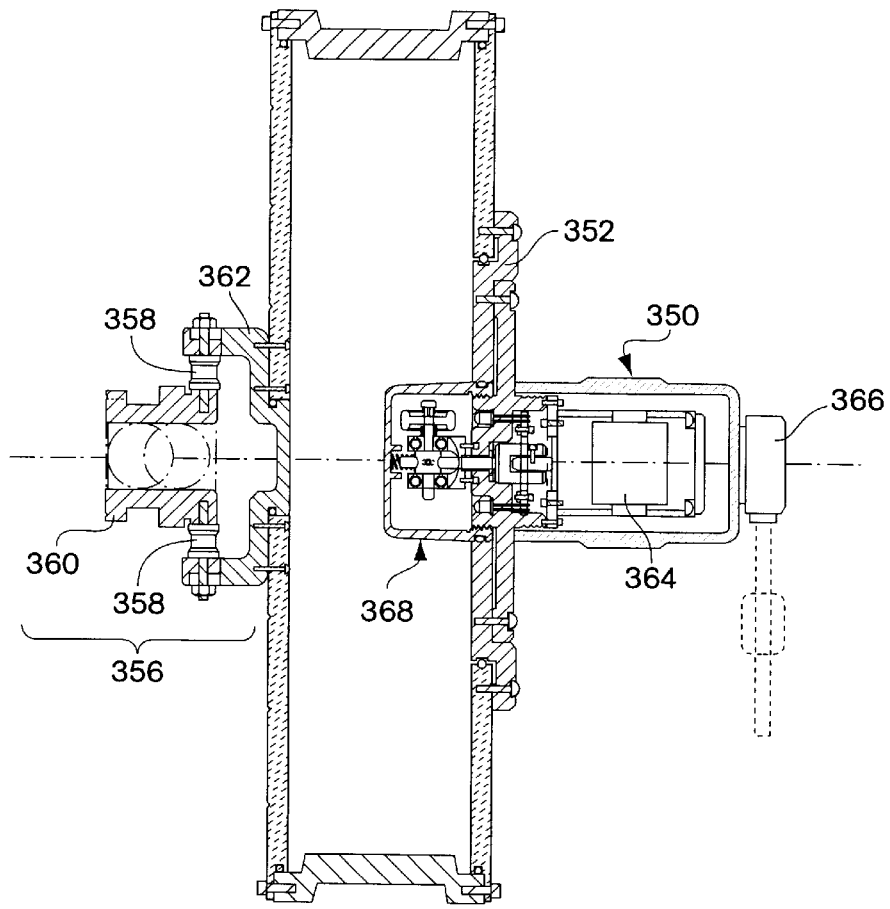
FIG. 12 is a cross-sectional view of a sample drum having a vibration device mounted thereon.

As shown in FIG. 12, the vibration device 350 is mounted to an adapter plate 352 which is mounted in the location normally occupied by the access cover. In order to permit vibration of sample drum 10 independently of the remainder of the apparatus, the sample drum is coupled to the hub rotor by a spring assembly 356. The spring assembly 356 may be implemented using elastomeric coupling elements 358 between a sample drum hub 360 and an adapter bracket 362. The sample drum hub 360 is locked to the hub rotor 62 (FIG. 1), and the adapter bracket 362 is attached to the sample drum 10. A 3-point elastomeric suspension may be utilized. The vibration device 350 includes a vibration motor 364 which receives electrical power through a slip ring connection 366. The slip ring connection 366 permits operation of the vibration device 350 as sample drum 10 rotates.

Figure 13:
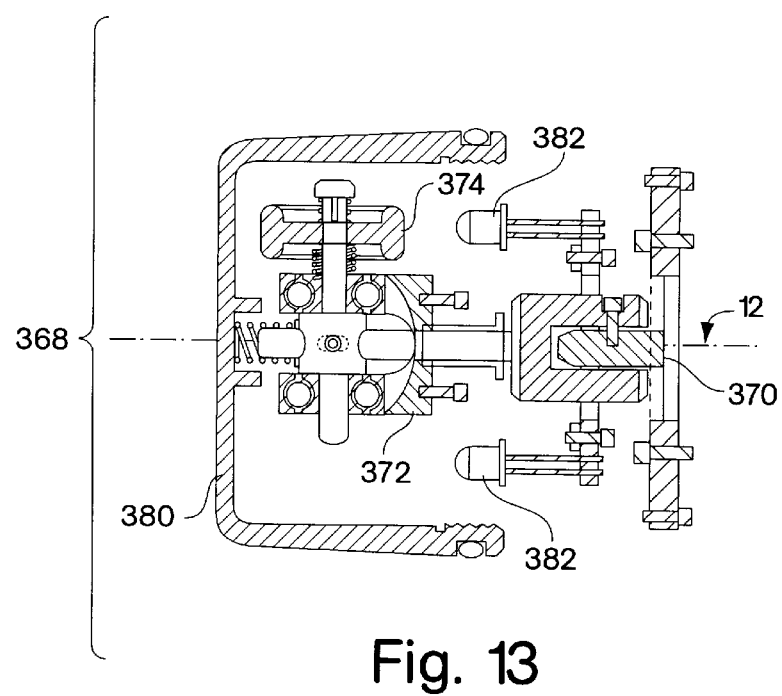
FIG. 13 is a detail of a portion of the vibration device shown in FIG. 12.

A detail of an oscillator head portion 368 of the vibration device 350 is shown in FIG. 13. Shaft 370 of vibration motor 364 is connected to an oscillator assembly which includes a 2-cycle end CAM 372 that produces oscillation parallel to axis 12. The oscillator assembly further includes an eccentric load 374 which induces oscillation perpendicular to axis 12. The vibration amplitude may be increased by increasing the speed of vibration motor 364 which in turn extends the distance of eccentric load 374 from the center shaft by the increase in centrifugal force. This permits the vibration amplitude to be controlled by changing the drive frequency or speed. The oscillator head portion 368 includes a cover 380, which may be transparent, and may include light emitting diodes 382 for illuminating the sample chamber.

While there have been shown and described what are at present considered the preferred embodiments of the present invention, it will be obvious to those skilled in the art that various changes and modifications may be made therein without departing from the scope of the invention as defined by the appended claims.

What is claimed is:

1. Apparatus for determining flowability of a powder by sensing powder avalanching, comprising:
    a sample drum having a central axis and a generally cylindrical sample chamber for holding a powder sample that partially fills the sample chamber;
    a support frame including a drum shaft for supporting said drum with said central axis generally horizontal;
    a drive motor;
    a drive mechanism coupled between said drive motor and said drum shaft such that said drum rotates about said central axis when said drive motor is energized, wherein gravity causes avalanching of the powder sample at intervals as said sample drum rotates; and
    a torque loading sensor for sensing variations in torque loading in said drive mechanism caused by the avalanching of the powder sample and for sensing powder sample position within the sample chamber as said sample drum rotates and for producing in response thereto an electrical signal that is representative of the powder sample position and the avalanching of the powder sample.

2. Apparatus for determining flowability of a powder as defined in claim 1 wherein said drive mechanism comprises first and second pulleys respectively mounted on said drive motor and said drum shaft, and a drive belt connected between said first and second pulleys and wherein said torque loading sensor comprises a load cell for sensing tension in said drive belt.

3. Apparatus for determining flowability of a powder as defined in claim 1 further comprising a humidity sensor in fluid communication with the sample chamber of said sample drum for sensing the humidity level in the sample chamber.

4. Apparatus for determining flowability of a powder as defined in claim 1 further comprising a gas conditioning system for controllably circulating a gas through said sample chamber during rotation of said sample drum.

5. Apparatus for determining flowability of a powder by sensing powder avalanching, comprising:
    a sample drum having a central axis and a generally cylindrical sample chamber for holding a powder sample that partially fills the sample chamber;
    a support frame including a drum shaft for supporting said drum with said central axis generally horizontal;
    a drive motor;
    a drive mechanism coupled between said drive motor and said drum shaft such that said drum rotates about said central axis when said drive motor is energized wherein gravity causes avalanching of the powder sample at intervals as said sample drum rotates;
    an avalanche sensor for sensing the avalanching of the powder sample within the sample chamber as said sample drum rotates and for producing in response thereto an electrical signal that is representative of the avalanching of said powder sample; and
    a gas conditioning system in fluid communication with the sample chamber of said sample drum for controllably circulating a gas through the sample chamber.

6. Apparatus for determining flowability of a powder as defined in claim 5 wherein said gas conditioning system includes a humidity sensor for sensing the humidity level in said sample chamber.

7. Apparatus for determining flowability of a powder as defined in claim 6 wherein said gas conditioning system includes means for controlling the humidity level of the gas in said sample chamber.

8. Apparatus for determining flowability of a powder as defined in claim 6 wherein said gas conditioning system includes means for controlling the temperature of the gas in said sample chamber.

9. Apparatus for determining the flowability of a powder by sensing powder avalanching, comprising:
    a sample drum having a central axis and a generally cylindrical sample chamber for holding a powder sample that partially fills the sample chamber;
    a support frame including a drum shaft for supporting said drum with said central axis generally horizontal;
    a drive motor;
    a drive mechanism coupled between said drive motor and said drum shaft such that said drum rotates about said central axis when said drive motor is energized, wherein gravity causes avalanching of the powder sample at intervals as said sample drum rotates; and
    an avalanche sensor, which is operable without transmission of light through a wall of the sample chamber, for sensing the avalanching of the powder sample within the sample chamber as said sample drum rotates and for producing in response thereto an electrical signal that is representative of the avalanching of the powder sample.

10. Apparatus as defined in claim 9 wherein said avalanche sensor comprises a backlash sensor for sensing intermittent reverse angular displacement of said sample drum caused by avalanching of the powder sample within the sample chamber as said drum rotates and for producing said electrical signal in response thereto.

11. Apparatus as defined in claim 9 wherein said avalanche sensor comprises a torque-loading sensor for sensing variations in torque loading in said drive mechanism caused by the avalanching of the powder sample and for sensing powder sample position within the sample chamber as said sample drum rotates and for producing said electrical signal in response thereto.

12. Apparatus as defined in claim 9 wherein said avalanche sensor comprises an energy beam scanner for directing an energy beam radially outwardly from the central axis of the sample chamber and for sensing a reflected energy beam, said energy beam scanner providing said electrical signal in response to said reflected energy beam, and a scanner for rotating said energy beam about said central axis relative to said drum.

* * * * *